(12) United States Patent
Liu et al.

(10) Patent No.: US 9,863,933 B2
(45) Date of Patent: Jan. 9, 2018

(54) METHOD FOR DETERMINING THE REPAIR ACTIVITY OF NON-HOMOLOGOUS END JOINING

(71) Applicant: Soochow University, Suzhou, Jiangsu (CN)

(72) Inventors: Fenju Liu, Jiangsu (CN); Jie Du, Jiangsu (CN); Jiahua Yu, Jiangsu (CN); Haowen Zhang, Jiangsu (CN); Zengfu Shang, Jiangsu (CN); Yushuo Zhang, Jiangsu (CN)

(73) Assignee: SOOCHOW UNIVERSITY, Suzhou (CN)

( * ) Notice: Subject to any disclaimer, the term of this patent is extended or adjusted under 35 U.S.C. 154(b) by 0 days.

(21) Appl. No.: 15/310,491

(22) PCT Filed: Aug. 18, 2015

(86) PCT No.: PCT/CN2015/087321
§ 371 (c)(1),
(2) Date: Nov. 11, 2016

(87) PCT Pub. No.: WO2017/024602
PCT Pub. Date: Feb. 16, 2017

(65) Prior Publication Data
US 2017/0254799 A1    Sep. 7, 2017

(30) Foreign Application Priority Data
Aug. 7, 2015   (CN) .......................... 2015 1 0478296

(51) Int. Cl.
| | | |
|---|---|---|
| *C12N 5/00* | (2006.01) | |
| *G01N 33/50* | (2006.01) | |
| *C12Q 1/44* | (2006.01) | |
| *C12N 15/90* | (2006.01) | |
| *C12N 15/11* | (2006.01) | |

(52) U.S. Cl.
CPC .......... *G01N 33/502* (2013.01); *C12N 15/11* (2013.01); *C12N 15/907* (2013.01); *C12Q 1/44* (2013.01); *G01N 33/505* (2013.01); *C12N 2310/14* (2013.01); *C12N 2310/20* (2017.05)

(58) Field of Classification Search
None
See application file for complete search history.

(56) References Cited

FOREIGN PATENT DOCUMENTS

| | | |
|---|---|---|
| CN | 103388006 A | 11/2013 |
| CN | 104673816 A | 6/2015 |
| WO | 2012021632 A2 | 2/2012 |
| WO | 2012138927 A2 | 10/2012 |

*Primary Examiner* — Celine Qian
(74) *Attorney, Agent, or Firm* — SZDC Law P.C.

(57) ABSTRACT

The invention discloses a method for determining the repair activity of NHEJ. In this method, HPRT gene is mutated by using a site-directed gene mutation technology, and plasmid transfection, and 6-TG treatment are performed. By means of the method of the invention, the NHEJ repair activity level of cells can be observed by measuring the cell viability. The method can be used for screening the effects of different drugs and different genes on the NHEJ repair activity.

8 Claims, 2 Drawing Sheets

SEQUENCE LISTING

<160> NUMBER OF SEQ ID NOS: 5

<210> SEQ ID NO 1
<211> LENGTH: 14
<212> TYPE: DNA
<213> ORGANISM: Artificial Sequence
<220> FEATURE:
<223> OTHER INFORMATION: DNA sequence of a left-arm recognition sequence

<400> SEQUENCE: 1
atgaccttga ttta                                                    14

<210> SEQ ID NO 2
<211> LENGTH: 14
<212> TYPE: DNA
<213> ORGANISM: Artificial Sequence
<220> FEATURE:
<223> OTHER INFORMATION: DNA sequence of a right-arm recognition
      sequence

```
<400> SEQUENCE: 2
ccaaatcctc agca                                                         14

<210> SEQ ID NO 3
<211> LENGTH: 27
<212> TYPE: DNA
<213> ORGANISM: Artificial Sequence
<220> FEATURE:
<223> OTHER INFORMATION: DNA sequence of a forward primer

<400> SEQUENCE: 3
aaacaccgaa agggtgttta ttcctca                                           27

<210> SEQ ID NO 4
<211> LENGTH: 28
<212> TYPE: DNA
<213> ORGANISM: Artificial Sequence
<220> FEATURE:
<223> OTHER INFORMATION: DNA sequence of a reverse primer

<400> SEQUENCE: 4
ctctaaaact gaggaataaa caccctttt                                         28

<210> SEQ ID NO 5
<211> LENGTH: 21
<212> TYPE: DNA
<213> ORGANISM: Artificial Sequence
<220> FEATURE:
<223> OTHER INFORMATION: DNA sequence of DNA-PKcs siRNA

<400> SEQUENCE: 5
uucuccgaac gugucacgut t                                                 21
```

METHOD FOR DETERMINING THE REPAIR ACTIVITY OF NON-HOMOLOGOUS END JOINING

This application is a national phase application of PCT/CN2015/087321, filed on Aug. 18, 2015, which claims priority to Chinese Patent Application No.: CN 201510478296.2, entitled "method for determining the repair activity of non-homologous end joining," filed on Aug. 7, 2015, all of which are incorporated by reference for all purposes as if fully set forth herein.

FIELD OF THE INVENTION

The invention relates to the field of molecular biology, and more particularly to a method for determining the repair activity of non-homologous end joining.

DESCRIPTION OF THE RELATED ART

The non-homologous end joining (NHEJ) is a repair pathway of cell DNA double-strand breaks. This repair process can directly reconnect two broken DNA terminals, without the participation of any template chromosome. However, different from another repair pathway of homologous recombination (HR), the NHEJ repair is generally accompanied with the insertion or deletion of nucleotide, and thus the gene function is lost due to gene mutation.

The integrity of DNA which is a keeper of genetic information is of great importance to cells. Various endogenous or exogenous factors can cause damage to cell genome DNA, and there are complex repair systems in cells responding to different damages. As the most serious and lethal damage, the DNA double-strand breaks (DSBs) will lead to cell death if it is not repaired in time. In clinical treatment of tumors, radiotherapy and a majority of chemotherapeutic drugs may cause DSBs of tumor cells, and the tumor cells mainly repair the broken DNA double strands through NHEJ repair and HR repair, wherein NHEJ is independent of cell-cycle and represents a main way for repairing intracellular DSBs, and the activity of NHEJ determines the sensitivity of tumor cells to ionizing radiation and chemotherapeutic drugs to some extent. When the repair activity of NHEJ in tumor cells is inhibited, the effects of radiotherapy and chemotherapy can be greatly improved.

Currently, the methods available for determining the NHEJ activity mainly include staining of specific proteins γH2AX and 53BP1 of DNA double-strand breaks, neutral comet assay of broken DNA fragments, and study of NHEJ activity using relatively complex molecular biology methods. For example, a reporter plasmid is designed for NHEJ repair activity based on meganuclease I-SceI, and transfected into cells to screen the stable expression cell lines, then I-SceI nuclease is introduced to induce DSBs, and finally the fluorescent expression of the reporter plasmid is observed to determine the repair capability of NHEJ (Identification of Novel Radiosensitizers in a High-Throughput, Cell-Based Screen for DSB Repair Inhibitors, Alexander G, Molecular Cancer Therapeutics, Vol. 14, P326-342, 2015 (2)). However, the above methods are complex and include many steps, and staining and screening of specific cell lines are needed.

Currently the site-directed genome editing technologies are developed rapidly and now mainly include the following three types, Zinc finger nucleases (ZFNs), transcription activator-like effector nucleases (TALENs), and clustered regularly interspaced short palindromic repeats (CRISPR)/CRISPR associated protein 9 (Cas9). In these technologies, the genome can be cut at specific DNA sites, and site-directed gene editing can be achieved by inducing NHEJ or HR repair. Also, these methods have high mutation efficiency, simple operation and low cost. By using the site-directed genome editing technology, the repair activity of NHEJ could be conveniently determined.

SUMMARY OF THE INVENTION

In order to solve the above technical problem, an object of the invention is to provide a method for determining the repair activity of NHEJ.

Hypoxanthine-guanine phosphoribosyltransferase (HPRT) participates in the salvage pathway of intracellular biosynthesis of purine nucleotide. 6-thioguanine (6-TG) could be incorporated into DNA by the catalytic activity of HPRT, therefore DNA synthesis and cell proliferation is inhibited.

If DSBs are introduced in a HPRT gene by using the above site-directed gene editing technology, the HPRT gene is mutated by NHEJ repair. HPRT mutant cells can survive in a culture medium containing 6-TG, and non-mutant cells cannot survive. Thus, the number and viability of the cells reflect the NHEJ repair level.

The principle of the invention is in that, DSB is induced in the HPRT gene by a site-directed gene mutation technology (ZFN, TALEN or CRISPR/Cas9), when NHEJ repair occurs at the broken site of the HPRT gene, the gene is mutated and the intracellular HPRT function is deactivated. When cells are cultured in a medium containing 6-TG, the 6-TG is incorporated into DNA by HPRT to cause cell death, however, the mutant cells arisen from the NHEJ repair are resistant to the toxicity of 6-TG due to the function inactivation of HPRT gene. Thus, the NHEJ repair activity of cells can be obtained by detecting the cell viability.

For the above purpose, the invention utilizes the following the technical solutions:
a method for determining the repair activity of non-homologous end joining comprising the steps of:
(1) constructing a plasmid for HPRT gene by using a TALEN technology or CRISPR/Cas9 technology;
(2) treating a mammalian cell combined with the constructed plasmid of the step (1) with an NHEJ (non-homologous end joining) inhibitor;
(3) culturing the mammalian cell of the step (2) in a DMEM culture medium containing 6-TG; and
(4) adding a MTT solution into the treated mammalian cells of the step (3), dissolving the formed blue formazan particles with DMSO, and then determining the light absorption value at OD570 nm via a microplate reader.

In an embodiment, in the step (1) when the plasmid for the HPRT gene is constructed by using the TALEN technology, a left-arm recognition sequence of the target gene is shown in SEQ ID NO:1, and the right-arm recognition sequence of the target gene is shown in SEQ ID NO:2.

In another embodiment, in step (1) when the plasmid for the HPRT gene is constructed by using the CRISPR/Cas9 technology, a forward primer sequence is shown in SEQ ID NO:3, and a reverse primer sequence is shown in SEQ ID NO:4.

In an embodiment, the mammalian cell of the step (2) is a 293T cell line, the NHEJ inhibitor is NU7441 or the siRNA of the NHEJ repair molecule DNA-PKcs, and sequence of the DNA-PKcs siRNA is shown in SEQ ID NO:5.

In a preferable embodiment, the step (2) specifically comprises transfecting the constructed plasmid of the step (1) into the 293T cell, and treating the transfected 293T cell with the DNA-PKcs inhibitor NU7441.

In another preferable embodiment, the plasmid transfection in the step (2) comprises inoculating the 293T cell in a culture dish, and transfecting the constructed plasmid of the step (1) into the 293T cell by using Lipofectamine 3000 as a transfection reagent when the cell density reaches 70%.

In a preferable embodiment, the step (2) comprises co-transfecting the constructed plasmid of the step (1) and the DNA-PKcs siRNA into the 293T cell.

In another embodiment, the co-transfection of the step (2) includes inoculating the 293T cell in a culture dish, and co-transfecting the constructed plasmid of the step (1) and DNA-PKcs siRNA into the 293T cell by using Lipofectamine 3000 as a transfection reagent when the cell density reaches 70%.

By means of the above technical solutions, as compared with the prior methods the invention has the following advantages: in the invention HPRT gene is mutated by using a site-directed gene mutation technology, and plasmid transfection, drug treatment and 6-TG treatment are performed, and finally the repair activity of NHEJ is observed by detecting the cell viability. By means of the method of the invention, the NHEJ repair activity level of cells can be observed by measuring the cell viability. The method of the invention can be used for screening the effects of different drugs and different genes on the NHEJ repair activity and determining the responses of different cell lines to NHEJ-activity inhibiting drugs and genes, hence drugs and genes which could enhance sensitivities to chemotherapy and radiotherapy can be found.

DESCRIPTION OF THE PREFERRED EMBODIMENTS

Figure 1:
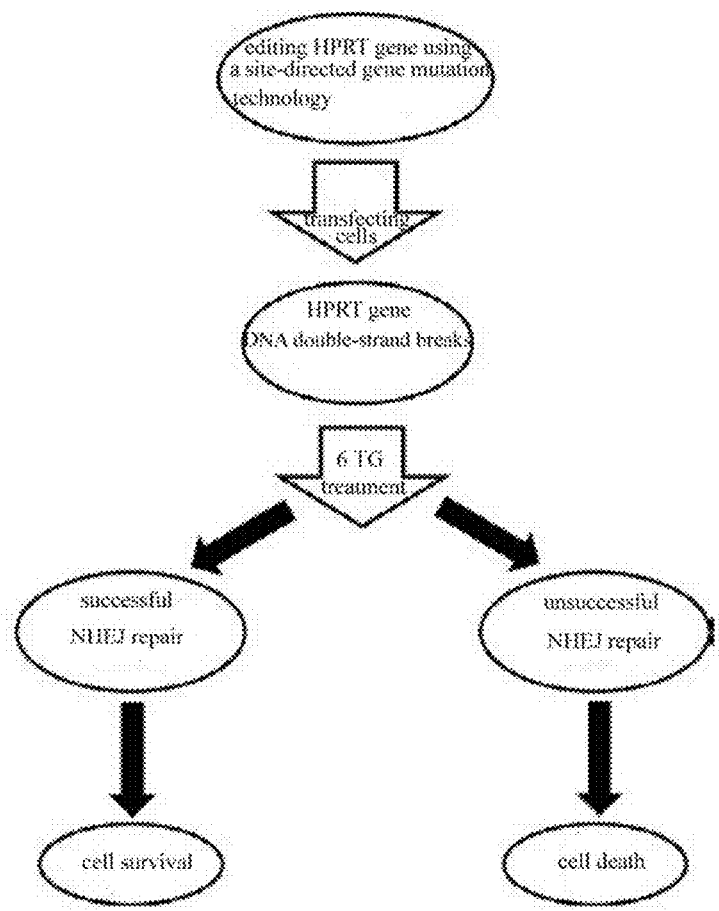
FIG. 1 is a schematic drawing illustrating the method for determining the NHEJ activity according to the invention.

The invention will be further illustrated in more detail with reference to accompanying drawings. It is noted that, the following embodiments only are intended for purposes of illustration and are not intended to limit the scope of the invention. In the following specific embodiments, the TALEN construction kit is available from SidanSai Biotechnology Co., Ltd., the CRISPR/Cas9 construction kit is available from Viewsolid Biotech Co. Ltd., the NHEJ inhibitor NU7441 is available from Selleck Co., Ltd., the DNA-PKcs siRNA is synthesized by GenePharma Co., Ltd. The primer is synthesized by Shanghai Branch Office of Invitrogen and is prepared into 10 µmol/L with distilled water. The transfecting reagent Lipofectamine 3000 is available from the Shanghai Branch Office of Invitrogen. MTT is available from Shanghai Sangon Biological Engineering Co., Ltd.

Embodiment 1

The inhibiting effects of different concentrations of NU7441 on NHEJ are determined by using the TALEN technology, and the specific steps are as follows:

(1) a TALEN plasmid for HPRT gene was constructed. The specific steps comprise: a left-arm recognition sequence ATGACCTTGATTTA (SEQ ID NO:1) and a right-arm recognition sequence CCAAATCCTCAGCA (SEQ ID NO:2) of the target HPRT gene were designed according to the TALEN design principle, and the two recognition sequences were inserted into a corresponding backbone carrier according to the method indicated on the TALEN construction kit. Competent E. coli cells were transformed with the carrier, uniformly spread on a kanamycin-resistant (20 µg/ml) plate and cultured in an incubator at 37° C. for 12-16 h, then 3-5 clones were selected and inoculated in 5 ml LB culture solution (containing 20 µg/ml kanamycin), and cultured in a shaker at 250 rpm under 37° C. for 16 h, plasmids were extracted and sequenced, and the obtained sequences were compared with the designed recognition sequences, ensuring the left-arm and right-arm TALEN plasmids with correct sequences were obtained.

(2) the left-arm and right-arm TALEN plasmids were transfected into 293T cells. The specific steps comprise: 293T cells were inoculated into a culture dish of 6 cm, and 4 µg left-arm plasmids and 4 µg right-arm plasmids were transfected into the 293T cells by using Lipofectamine 3000 when cell density reached 70%.

(3) the 293T cells were treated with different concentrations of the inhibitor NU7441. The specific steps comprise: the cells were inoculated into a 96-well plate after the TALEN plasmids were transfected into the cells for 24 h, and then the cells were treated with 0, 0.1, 0.5, 1.0 and 2.0 µmol/L NU7441 for 4 h respectively after cell attachment.

(4) the cells were treated with 6-TG. The specific steps comprise: the 293T cells were cultured in a DMEM culture medium containing 30 µmol/L 6-TG for 72 h after the NU7441 treatment.

(5) cell viability was determined by a MTT method. The specific steps comprise: a MTT solution was added after the treatment was completed, 2 h later, the formed blue formazan particles were dissolved with DMSO, and then the light absorption value of each well was determined at OD570 nm via a microplate reader. The cell viability reflects the repair activity of NHEJ, and for the blank control group the NHEJ activity was set as 100%.

Figure 2:
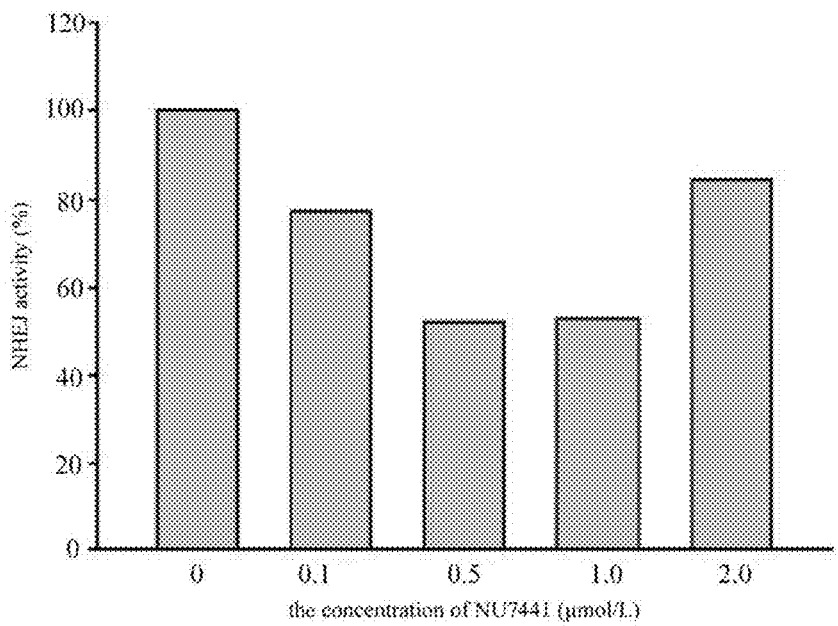
FIG. 2 shows the effects of different concentrations of NU7441 on the NHEJ repair activity according to the invention.

The experimental result is shown in FIG. 2. For the 293T cells, when the cells were treated with 0.5, 1.0 µmol/L NU7441 for 4 h, the inhibiting effect on the NHEJ repair activity was optimal, and the inhibition rate was about 50%. When the concentration of NU7441 was increased to 2.0 µmol/L, the inhibiting effect was reduced.

Embodiment 2

The time dependence of the inhibiting effect of 2.0 µmol/L NU7441 on NHEJ was determined by using the CRISPR/Cas9 technology, specific steps were as follows:

(1) a Cas9/gRNA plasmid was constructed for HPRT gene. The specific steps comprise: a target site primer of HPRT was designed according to a gRNA design principle, wherein the forward primer is AAACACCGAAAGGGT-GTTTATTCCTCA (SEQ ID NO:3), and the reverse primer is CTCTAAAACTGAGGAATAAACACCCTTT (SEQ ID NO:4). The primers were annealed to form a dimer, and the gRNA-sequence primer dimer was inserted into a Cas9/ gRNA plasmid according to the method indicated on the CRISPR/Cas9 construction kit. Competent *E. coli* cells were transformed with the plasmid, spread on an ampicillin-resistant plate. 3-5 clones were selected and cultured in a shaker, plasmids were extracted and sequenced, and the obtained sequences were compared with the designed recognition sequences, ensuring the Cas9/gRNA plasmids with correct sequences were obtained.

(2) the Cas9/gRNA plasmids were transfected into 293T cells. The specific steps comprise: 293T cells were inoculated into a 6 cm culture dish, and 5 μg Cas9/gRNA plasmid was transfected into the 293T cells by using Lipofectamine 3000 when cell density reached 70%.

(3) the 293T cells were treated with 2.0 μmol/L NU7441. The specific steps comprise: the cells were inoculated into a 96-well plate after the Cas9/gRNA plasmid was transfected into the cells for 24 h, and then the cells were treated with 2.0 μmol/L NU7441 for 0, 0.5, 1, 2 and 4 h respectively after cell attachment.

(4) the cells were treated with 6-TG. The specific steps comprise: the 293T cells were cultured in a DMEM culture medium containing 30 μmol/L 6-TG for 72 h after the NU7441 treatment.

(5) cell viability was determined by a MTT method. The specific steps comprise: a MTT solution was added after the treatment was completed, 2 h later, the formed blue formazan particles were dissolved with DMSO, and then the light absorption value of each well was determined at OD570 nm via a microplate reader. The cell viability reflects the repair activity of NHEJ, and for the blank control group the NHEJ activity was set as 100%.

Figure 3:
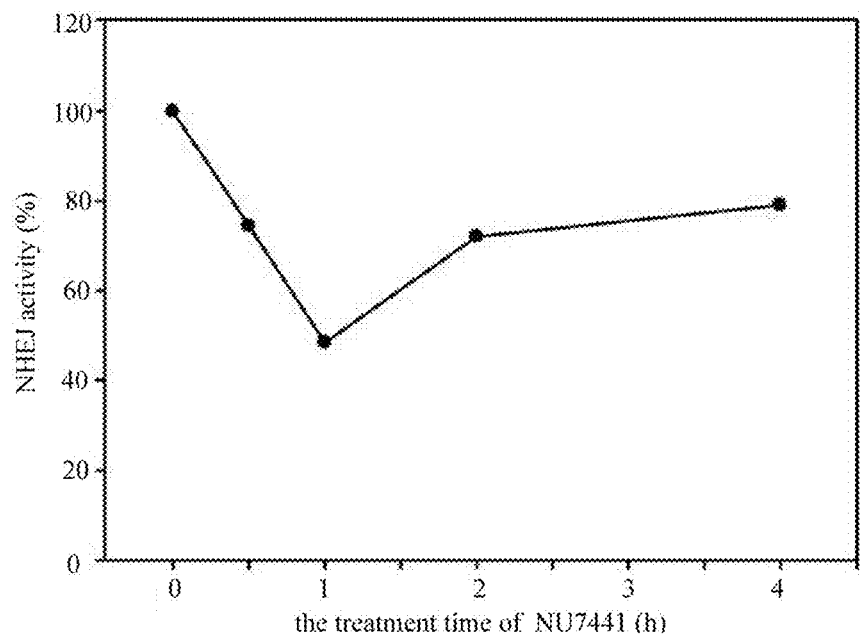
FIG. 3 shows the effects of 2.0 µmol/L NU7441 on the NHEJ repair activity for different treatment time according to the invention.

The experimental result is shown in FIG. 3. For the 293T cells, when the cells were treated with 2.0 μmol/L NU7441 for 1 h, the inhibiting effect on the NHEJ repair activity is optimal, and the inhibition rate was about 50%, and then the inhibiting effect on the NHEJ activity is reduced over time.

Embodiment 3

The inhibiting effect of DNA-PKcs siRNA on NHEJ was determined by using a CRISPR/Cas9 technology, and the specific steps comprise:

(1) a Cas9/gRNA plasmid was constructed for HPRT gene, and the specific steps are as described in the embodiment 2.

(2) the Cas9/gRNA plasmid and DNA-PKcs siRNA were co-transfected into 293T cells. The specific steps comprise: 293T cells were inoculated into a culture dish of 6 cm, and 3 μg Cas9/gRNA plasmid and 3 μg DNA-PKcs siRNA were co-transfected into the 293T cells by using Lipofectamine 3000 when cell density reached 70%, and a negative control siRNA was transfected for the negative control group. The gene sequence of DNA-PKcs siRNA was UUCUC-CGAACGUGUCACGUTT (SEQ ID NO:5).

(3) the cells were treated with 6-TG. The specific steps comprise: the cells were inoculated into a 96-well plate after the transfection is performed for 24 h, then the culture medium was replaced with a DMEM culture medium containing 30 μmol/L 6-TG after cell attachment, and the cells were continually cultured for 72 h.

(4) cell viability was determined by a MTT method. The specific steps comprise: a MTT solution was added after the treatment was completed, 2 h later, the formed blue formazan particles were dissolved with DMSO, and then the light absorption value of each well was determined at OD570 nm via a microplate reader. The cell viability reflects the repair activity of NHEJ, and for the control group the NHEJ activity was set as 100%.

Figure 4:
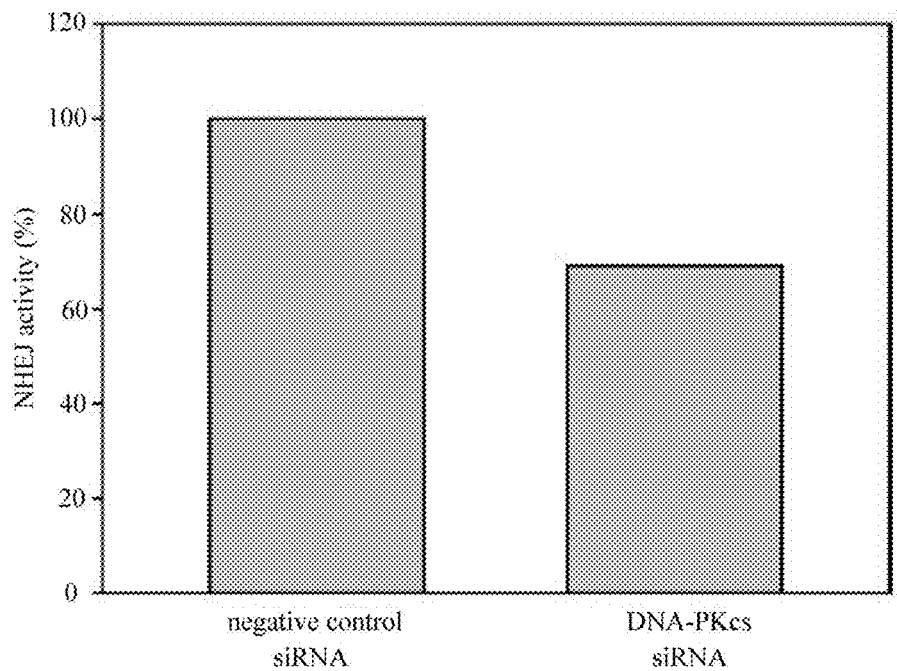
FIG. 4 shows the effects of DNA-PKcs siRNA transfection on the NHEJ repair activity.

The experimental result is shown in FIG. 4. It is indicated that after the expression of the DNA-PKcs was reduced by siRNA transfection, the repair activity of NHEJ was inhibited significantly in the 293T cells.

In conclusion, by means of the method of the invention, the repair activity level of NHEJ of cells can be observed by measuring the cell viability. In such a method, HPRT gene is mutated by using a site-directed gene mutation technology, and plasmid transfection, and 6-TG treatment are performed. The method of the invention can be used for screening chemical NHEJ inhibitors and genes involved in mediating NHEJ activity.

The above preferred embodiments are described for illustration only, and are not intended to limit the scope of the invention. It should be understood, for a person skilled in the art, that various improvements or variations can be made therein without departing from the spirit and scope of the invention, and these improvements or variations should be covered within the protecting scope of the invention.

What is claimed is:

1. A method for determining the repair activity of non-homologous end joining, comprising steps of:
   (1) constructing a plasmid for HPRT gene by using a TALEN technology or CRISPR/Cas9 technology;
   (2) treating a mammalian cell combined with the constructed plasmid of the step (1) by an NHEJ inhibitor;
   (3) culturing the mammalian cell of the step (2) in a culture medium containing 6-thioguanine;
   (4) adding a MTT solution into the treated mammalian cell of the step (3) to form blue formazan particles, dissolving the formed blue formazan particles and then determining the light absorption value thereof at OD570 nm via a microplate reader; and
   (5) determining the repair activity of non-homologous end joining based on the light absorption value.

2. The method as claimed in claim 1, wherein in the step (1) when the plasmid for the HPRT gene is constructed using the TALEN technology, the plasmid for the HPRT gene is constructed using a left-arm recognition sequence of a target gene shown in SEQ ID NO:1 and a right-arm recognition sequence of the target gene shown in SEQ ID NO:2.

3. The method as claimed in claim 1, wherein in the step (1) when the plasmid for the HPRT gene is constructed using the CRISPR/Cas9 technology, the plasmid for the HPRT gene is constructed using a forward primer sequence shown in SEQ ID NO:3 and a reverse primer sequence shown in SEQ ID NO:4.

4. The method as claimed in claim 1, wherein the mammalian cell of the step (2) is a 293 cell, the NHEJ inhibitor is NU7441 or DNA-PKcs siRNA, and the sequence of the DNA-PKcs siRNA is shown in SEQ ID NO: 5.

5. The method as claimed in claim 4, wherein the step (2) comprises transfecting the constructed plasmid of the step (1) into the 293T cell, and treating the transfected 293 T cell with the NHEJ inhibitor NU7441.

6. The method as claimed in claim 5, wherein the plasmid transfection in the step (2) comprises inoculating the 293T cell in a culture dish, and transfecting the constructed plasmid of the step (1) into the 293T cell by using Lipofectamine 3000 as a transfection reagent when the cell density reaches 70%.

7. The method as claimed in claim 4, wherein the step (2) comprises co-transfecting the constructed plasmid of the step (1) and the DNA-PKcs siRNA into the 293T cell.

8. The method as claimed in claim 7, wherein the co-transfection of the step (2) comprises inoculating the 293T cell in a culture dish, and co-transfecting the constructed plasmid of the step (1) and DNA-PKcs siRNA into the 293T cell by using Lipofectamine 3000 as a transfection reagent when the cell density reaches 70%.

* * * * *